United States Patent [19]

Freezer

[11] 4,175,556
[45] Nov. 27, 1979

[54] INHALER WITH FLOW-THROUGH CAP

[76] Inventor: Winthrop J. Freezer, 57 Hallam, San Francisco, Calif. 94103

[21] Appl. No.: 894,321

[22] Filed: Apr. 7, 1978

[51] Int. Cl.² .......................................... A61M 15/08
[52] U.S. Cl. ...................................... 128/198; 128/206
[58] Field of Search ............... 128/198, 201, 206, 208, 128/266; 131/170 A, 171 A, 261 A

[56] References Cited

U.S. PATENT DOCUMENTS

| 393,869 | 12/1888 | Warren | 128/201 |
| 2,641,255 | 6/1953 | Leonaitis | 128/206 |
| 3,046,983 | 7/1962 | Grubb et al. | 128/206 X |

FOREIGN PATENT DOCUMENTS

| 121498 | 6/1946 | Australia | 128/198 |
| 837389 | 6/1960 | United Kingdom | 128/206 |

*Primary Examiner*—Henry J. Recla

*Attorney, Agent, or Firm*—Joseph L. Strabala

[57] ABSTRACT

An inhaler with a flow-through cap and adjustment for controlling the concentration of a medicament when in use is fabricated from a hollow cylindrical barrel or cartridge having open top and bottom ends with an end plug threadedly received in the bottom end to both seal the bottom end and also, when loosened, to adjust the air flow into the bottom end of the barrel and a bullet-shaped nose cap with a blind bore threadedly received in the top end of the barrel, with the nose cap being equipped with a seal in the blind bore operable to seal off the top end of the barrel and also having a cross bore vent communicating with the blind bore allowing the medicament in the inhaler to be inhaled when the nose cap is loosened via the cross bore vent without removing the nose cap. The nose cap and end plug can be tightened on the barrel to provide adequate seals for more volatile medicaments, and of course, the unit is refillable when the medicament is exhausted.

8 Claims, 2 Drawing Figures

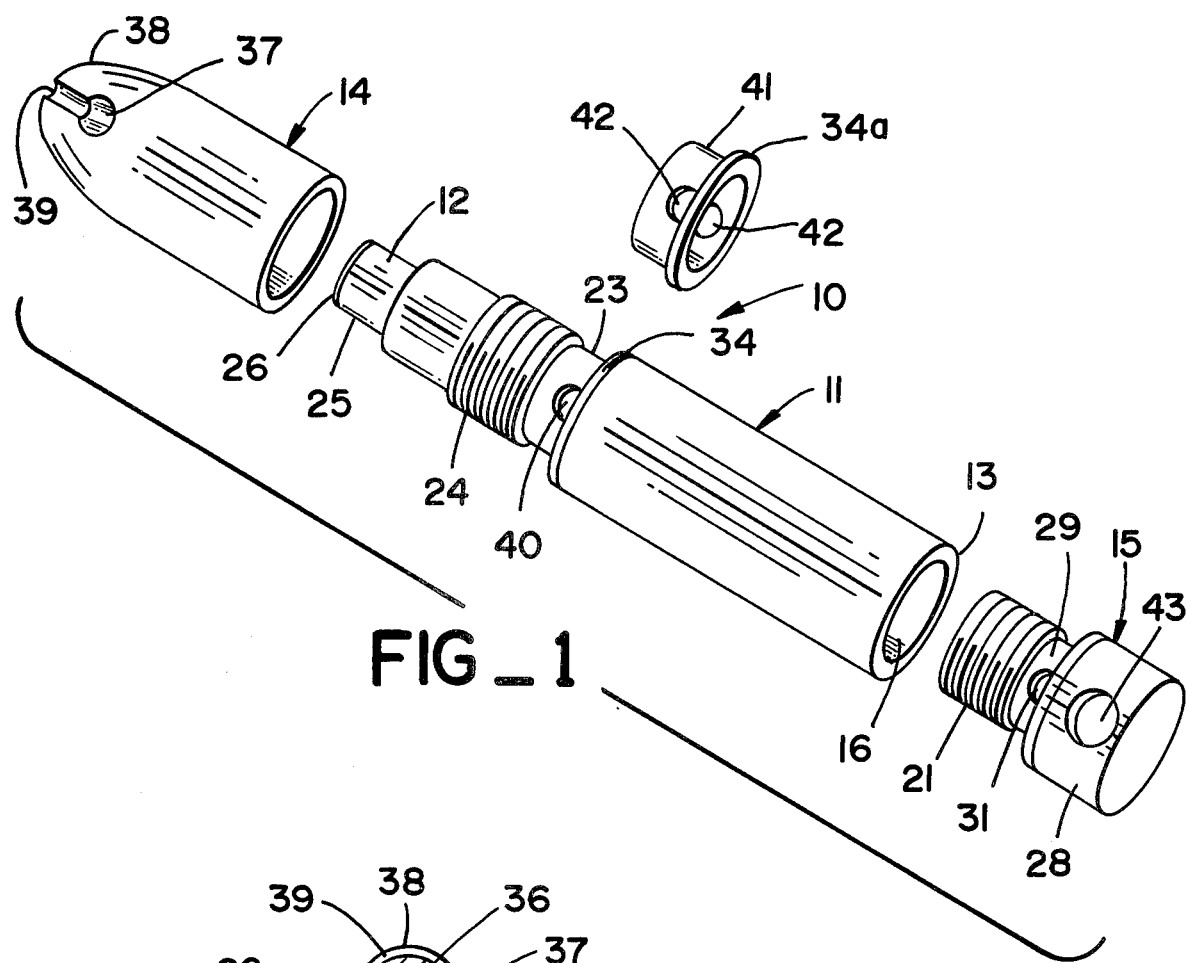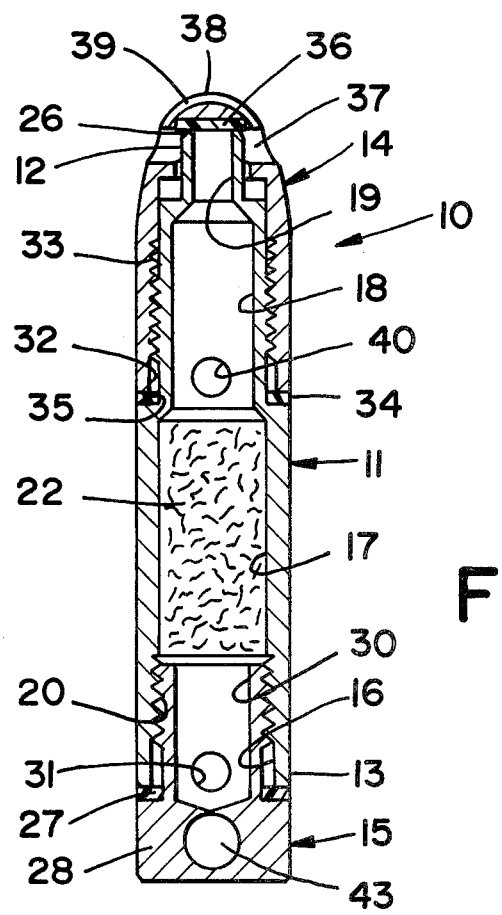

4,175,556

INHALER WITH FLOW-THROUGH CAP

BACKGROUND

Nasal inhalers have been available for a number of years to permit convenient inhalation of medicaments, such as benzedrine, ephedrine, menthol and camphor, often used to relieve nasal congestion associated with the common cold. In addition, when the inhalers have satisfactory seals and are properly constructed, they are also useful in dispensing vasodialators, sometimes used to treat heart patients, such as amyl nitrite and other short-chain alkyl nitrites.

Prior art nasal inhalers range from units employed to be used in a single nostril of the nose to units which have dual protuberances to be received in both nostrils simultaneously. Inhalers representative of the dual nostril type are shown in U.S. Pat. No. 3,724,459 issued to Congro and U.S. Pat. No. 3,255,750 issued to Schwartzman et al.

Basically, inhalers, whether constructed for single or dual nostril use, most often employ a cap which is required to be removed when the inhaler is in use, thereby uncovering an inhaling protuberance of the unit that is inserted in a nostril so that, upon inhalation by the user, air flow passes through a wadding material in the inhaler having an absorbed medicament, thereby carrying its concentrated vapors into the user's nasal passages and lungs. Most of these inhalers do not have the cap retained in any manner, such as the hinged construction shown in the aforementioned Congro patent. Further, the known prior art inhalers do not have fully adjustable means to control the air flow through the unit, whereby the concentration of the vapors of the medicament in the air flow can be precisely adjusted.

In addition, the prior art units are not constructed in a manner that they can be used for the more volatile inhalants, such as ammonia and the vasodialators mentioned above. Normally, ammonia and the vasodialators are often packaged in closed glass vials which are broken just prior to use to prevent inadvertent evaporation. However, with proper construction of the inhaler, it is possible to contain these more volatile inhalants which would otherwise rapidly evaporate. Of course, to contain such volatile inhalants, it is necessary that the inhaler unit not be vented to the atmosphere when not in use and also that it have adequate seals to prevent the loss of vapor from these substances.

OBJECTS OF THE INVENTION

An object of this invention is to provide an inhaler in which it is unnecessary to remove its cap when it is used, thereby preventing loss of the cap and also increasing the convenience to the user when the inhaler is employed.

Another object of the invention is the provision of a refillable inhaler in which the air flow therethrough can be precisely regulated by the user for a comfortable concentration of vapor inhaled.

Another object of the invention is the provision of an inhaler constructed so that it can be used with highly volatile inhalants without loss thereof from the unit when it is not in use.

Also, it is an object of the invention to provide a compact, convenient, serviceable inhaler useful for a wide variety of inhalants due to its design features and one which will ensure the user that such important medicaments such as the vasodialators used to treat infarctions are not inadvertently lost.

SUMMARY OF THE INVENTION

The above objects and others which will be apparent from the description herein can be accomplished by a tubular inhaler with a flow-through cap and flow adjustments including a cylindrical hollow barrel having open top and bottom ends with an internal compartment for absorbant means to store an inhalant, an end plug removably received in the bottom of the barrel operable to sealingly close the end of the barrel when fully inserted and having a vent means operable to control the air flow into the bottom of said barrel when the end plug is progressively removed and a bullet-shaped nose cap with a blind bore adjustably received on the top end of the barrel, the nose cap having internal sealing means located in the blind bore operable to close the top end of the barrel when the cap is fully received on the barrel, and also having a cross bore means which communicates with the blind bore, thereby allowing an air and inhalant vapor flow to be inhaled from inside the barrel through the nose cap when it is adjusted to open the top end of the barrel without the necessity of removing the nose cap.

DESCRIPTION OF THE DRAWINGS

The accompanying drawings show the preferred embodiment of the invention known to the applicant, and it is not intended that the invention be limited to the specific structures shown therein, wherein:

FIG. 1 is an exploded perspective of the novel inhaler showing its three principal components; and FIG. 2 is a vertical section through the assembled inhaler, better illustrating its internal construction.

DESCRIPTION OF THE PREFERRED EMBODIMENT

As can be seen by reference to FIGS. 1 and 2, the novel inhaler 10 of this invention is composed of three principal parts. The main component is a hollow cylindrical barrel 11 having an open top end 12 and an open bottom end 13 so that there is a continuous passage through the barrel. Assembled on the top end of the barrel is a bullet-shaped nose cap 14, and an end plug 15 is employed to close the bottom end of the barrel.

Internal construction of the barrel 11 is best illustrated in FIG. 2, showing a plurality of internal stepped bores 16, 17, 18 and 19 which are coaxially aligned and formed with progressively decreasing diameters from the bottom end to the top end of the barrel, thereby forming its hollow central passage. The larger bore 16 has internal threads 20 adjacent to the bottom end of the barrel, which receive the external threads 21 of the end plug 15. The next smaller bore 17 forms a chamber for the absorbant material, such as cotton wadding 22, employed to store an inhalant or medicament to be dispensed with the unit. The next two bores 18 and 19, of successive smaller diameter, complete the passage through the cylindrical barrel and are to some extent dictated by the external structures of the barrel which are associated with the cooperating nose cap 14. Bore 18, however, forms a mixing chamber for the air and vapors of the inhalant, which will be described in greater detail subsequently.

As can be seen in FIGS. 1 and 2, the outer surface of the barrel 11 at the top end is progressively stepped with sections of decreasing diameter toward its distal end, forming a neck section 23 having external threads 24 for receiving the nose cap 14 and a smaller tip section 25 with a chamfered distal end 26 that cooperates with the seal and the blind bore of the nose cap (hereinafter described) to close the top end of the barrel.

In FIG. 2, the end plug 15 is shown threadedly received in the bottom end 13 of the barrel 11 with a plastic seal washer 27 employed between the plug and the end of the barrel to obtain a tight positive seal when the inner surface of head 28 of the end plug forces the washer against the bottom end of the barrel. The shank 29 of the end plug which includes the external threads 21 is provided with an axial blind bore 30 which is intersected by a cross bore 31 (normal to the blind bore) that is located in the shank between the threads and its head, as best illustrated in FIG. 1. Normally, this cross bore is sized as desired to achieve the desirable vent feature or function accomplished by loosening the end plug.

When the end plug 15 is assembled with the barrel 11, as shown in FIG. 2, it supports the cotton wadding 22 in the inhalant chamber, identified as bore 17. Also, it can be appreciated that due to the construction of the plug, as it is progressively loosened (unscrewed) from the barrel, it can control and adjust the air flow into the bottom of the barrel via the cross bore since the mating threads between the plug and the barrel will not pass any substantial amount of air flow at the pressures involved. Of course, as air passes through the bottom end of the barrel and through the hollow passage thereof, it will necessarily flow through the cotton wadding, picking up the vapors of the inhalant stored thereon. By reducing the air flow into the bottom of the barrel by adjusting the end plug, the concentration of the vapors of the inhalant entrained in the air flow, of course, will be reduced. For example, when the device is used for ammonia, it is highly desirable to limit the concentration of its vapors to avoid extreme discomfort and possible injury to the user.

The construction of the bullet-shaped nose cap 14 provides the inhaler 10 with one of its unique characteristics, i.e., the ability to use the unit without removing the nose cap. The construction providing this feature is best illustrated in FIG. 2, wherein the nose cap is shown as having a blind bore 32 which includes internal threads 33 which are received on the external threads 24 of the barrel 11. When the nose cap is assembled on the end of the barrel, the open end thereof can compress a plastic washer seal 34 against a shoulder 35 of the barrel to form a tight seal. When the seal is effected between the nose cap and the shoulder on the barrel, a sealing disc 36 located in the bottom of the blind bore 32 is simultaneously forced against the chamfered end 26 of the tip section 25 of the barrel, thereby effectively sealing off its top end 12. A cross bore 37 is formed in the cap adjacent to the bottom end of the blind bore (near the top 38 of the cap) and arranged to intersect the blind bore in the area of the sealing disc.

As a result of this construction, the nose cap 14, when loosened to release the disc seal, will allow air flow containing vapors from the inhalant or medicament in the unit to pass out of the top end 12 into the barrel 11 via the cross bore 37 to the user without removing the cap from the barrel. Since the top 38 of the nose cap has a conical shape and the cross bore is located near the top of the cap, the passage of the air flow via the cross bore will not be obstructed by the fleshy portions of the nostril when the nose cap is inserted. Further, a groove 39 can be formed across the top of the cap, intersecting the cross bore, as illustrated in FIGS. 1 and 2, to ensure further unobstructed flow via this arrangement. In addition, it can be appreciated that the nose cap can be progressively loosened to adjust the air flow containing the vapors of the inhalant at the convenience of the user.

As shown in the drawings, an optional vent port 40 can be formed in barrel 11 which communicates with the mixing chamber, i.e., bore 18. The purpose of the vent port is to allow a flow of air into the central passage of the barrel when the end plug 15 has not been loosened to allow air to flow into the bottom of the unit, so the unit will still be functional. Of course, the vent port is sealed off by the nose cap 14 when it its open end is abutted against plastic washer 34. However, when the nose cap is loosened, air can flow into the annular channel between the bore 32 of the cap and the barrel, and into the mixing chamber via vent port 40. In the mixing chamber, air flowing via this passage will mix with the vapors of the inhalant and then be drawn out the top end 12 of the barrel and via the cross port 37 when the device is in use even though the end plug 15 has not been loosened to provide air flow from beneath the wadding 22. When certain highly volatile inhalants are employed, such as ammonia, their normal evaporation without air flow through the wadding may be sufficient to provide an adequate concentration of vapor in the mixing chamber for the user's comfort. Obviously, the size of the vent port 40 can be adjusted as desired.

To make the unit more flexible with a broader range of inhalants, the plastic seal washer 34 can be replaced with an alternate seal washer 34a having an integral sleeve 41 that is arranged to cover the vent port 40 (see FIG. 1). The sleeve includes a pair of ports 42 which can be brought into partial or complete registry with the vent port 40 by turning the washer 34a. In this manner, the air flow into the mixing chamber via vent port 40 can be precisely controlled or completely eliminated. As a result, when less volatile inhalants are employed with the unit, the vent port can be closed off and the end plug 15 loosened to provide air flow through the cotton wadding 22 to increase the concentration of the inhalant in the air flow egressing from cross port 37 in the nose cap 14.

Normally the plastic parts, usually formed of polypropylene, including washers 27, 34 and 34a and sleeve 41, can be stretched slightly to pass over the larger threaded sections when the unit is assembled.

As can be appreciated from the above description, the unique inhaler 10 described herein offers at least two separate means to control the air flow through the unit, whereby the concentration of the vapor in the inhalant can be precisely controlled. In addition, if desired, the construction can include the optional vent port 40 along with the ported sleeve unit to control air flow directly into the mixing chamber. Of course, all of the various adjustments on air flow are completely sealed off when the nose cap 14 and end plug 15 are respectively tightened on the barrel structure.

For convenience of the user, a bore 43 through the head 28 of the end plug 15 will accept a retaining lanyard to secure the device when important medicaments are contained in the inhaler, thereby preventing the inadvertent loss of the unit.

Having described my invention, I claim:

1. A tubular inhaler with a flow-through nose cap and having adjustments for controlling the concentration of a medicament dispensed when in use, comprising:

a cylindrical hollow barrel having open top and bottom ends with an internal compartment for absorbent means to store a medicament;

an end plug removably received in said bottom end of said barrel operable to sealingly close said bottom end of said barrel when fully inserted, said end plug having a vent means operable to control the flow of air into said bottom end of said barrel as said end plug is progressively removed; and a bullet-shaped nose cap with a blind bore adjustably received on the top end of said barrel, said nose cap having an internal sealing means located in said blind bore operable to close the top end of the barrel when said cap is fully received on said barrel and also having a cross-bore means which communicates with said blind bore, allowing air/vapor flow from inside said barrel through said nose cap when it is adjusted to open said top end of said barrel without removing the nose cap.

2. The tubular inhaler defined in claim 1 wherein the bullet-shaped nose cap has an arcuate groove across its top connecting to its cross bore means.

3. The tubular inhaler defined in claim 1 wherein the vent means in the end plug includes a port communicating through the end plug with hollow barrel that is closed off by said end plug until it is at least partially removed from said barrel.

4. The tubular inhaler defined in claim 1 wherein the barrel includes a vent port means covered by the nose cap communicating with the interior of said barrel operable to allow air flow into the barrel when said nose cap is loosened.

5. The tubular inhaler defined in claim 1 wherein sleeve means is employed with the vent port means and operable to control the air flow into the barrel via said vent port means when adjusted.

6. The tubular inhaler defined in claim 1 wherein the bullet-shaped nose cap has a conical top end and the cross bore means is located in a portion of reduced diameter of said nose cap.

7. The tubular inhaler defined in claim 1 wherein the end plug is threadedly received in the bottom end of the barrel.

8. The tubular inhaler defined in claim 1 wherein the bullet-shaped nose cap is threadedly received on the top end of the barrel.

* * * * *